United States Patent [19]

Arichika et al.

[11] Patent Number: 5,089,781
[45] Date of Patent: Feb. 18, 1992

[54] ELECTROMAGNETIC CONDUCTIVITY METER AND A CONDUCTIVITY MEASURING METHOD

[75] Inventors: Kenji Arichika, Ebina; Mitsuru Fukamachi, Yokohama; Satoshi Higashi, Ebina; Noboru Maruyama, Yachiyo, all of Japan

[73] Assignees: Tosoh Corporation, Tokyo; Nichiri Mfg. Co., Ltd., Chiba, both of Japan

[21] Appl. No.: 653,772

[22] Filed: Feb. 11, 1991

[30] Foreign Application Priority Data

Feb. 13, 1990 [JP] Japan .................. 2-29455

[51] Int. Cl.$^5$ ............................ G01N 27/02
[52] U.S. Cl. .................... 324/445; 324/204; 324/450
[58] Field of Search ............. 324/445, 450, 204, 438, 324/439, 453, 464; 73/25.02

[56] References Cited

U.S. PATENT DOCUMENTS

| 3,404,335 | 10/1968 | Kidder | 324/445 |
| 3,404,336 | 10/1968 | Rosenthal | 324/445 |
| 4,138,639 | 7/1977 | Hutchins | 324/445 |
| 4,740,755 | 4/1988 | Ogawa | 324/445 |

FOREIGN PATENT DOCUMENTS

| 60-190873 | 9/1985 | Japan. | |
| 983608 | 12/1982 | U.S.S.R. | 324/204 |

Primary Examiner—Kenneth A. Wieder
Assistant Examiner—Maura K. Regan
Attorney, Agent, or Firm—Ostrager & Chong

[57] ABSTRACT

An electromagnetic conductivity meter comprises a core; a primary coil wound around the core; an alternating power source for applying an alternating voltage having a given frequency to the primary coil to excite the core; a tube wound around the core through which a liquid to be measured flows; induction current detecting means disposed at the opposite ends of tube; and an operational means for determining the conductivity of the liquid to be measured from a value of the induction current detected by the induction current detection means.

4 Claims, 3 Drawing Sheets

ELECTROMAGNETIC CONDUCTIVITY METER AND A CONDUCTIVITY MEASURING METHOD

FIELD OF THE INVENTION

The present invention relates to an electromagnetic conductivity meter and a conductivity measuring method for measuring the conductivity of a liquid by using an electromagnetic induced current.

BACKGROUND OF THE INVENTION

Measurement of the conductivity of a liquid is often performed in an apparatus for treating a liquid such as liquid chromatograph or desalter. Conventional methods of measuring the liquid conductivity are mainly classified into an electrode method and an electromagnetic induction method.

FIG. 2 is a schematic view for explaining the principle of the two-electrode method. In the drawing, an alternating voltage is applied across electrodes 1, 1 from an alternating power source 2. The conductivity is determined in the two-electrode method by outputting via an operational amplifier 3 the amount of a current flowing across two electrodes 1, 1. It is also known a four-electrode method for measuring the conductivity by determining the voltage fall across two electrodes which are disposed between the electrodes 1 and 1.

Although these two-electrode and four-electrode methods have an advantage that a conductivity ranging from a very low value to a high value (0 to 10,000 $\mu$S/cm) can be measured, they have a disadvantage that so-called polarization resistance will not become zero because polarization occurs due to a reverse electromotive force caused by an electrolytic product on the surface of an electrode, a concentration gradient or a decrease in electrode reaction speed even if an alternating current is used.

An electromagnetic conductivity meter using an electro-magnetic induced current as shown in FIG. 3 has been known as second means for measuring the liquid conductivity (refer to Japanese Unexamined Publication Sho 60-190873).

In FIG. 3, a primary coil 6 and a detection coil 7 are wound around first and second excitation rings 4 and 5, respectively. An insulation loop tube 8 passes through the first and second excitation rings 4 and 5 and a liquid to be measured is introduced through the insulation loop tube 8. When an alternating voltage having a given amplitude and a given frequency is applied to the primary coil 6, the liquid in the insulation loop tube 8 serves as one turn coil so that an electromagnetically induced alternating current will flow through the liquid as represented by a dotted line. This causes an alternating electromotive current to be induced in the detection coil 7. The frequency of the induced alternating electromotive current is the same as the frequency of the voltage applied to the primary coil 6 and its amplitude is proportional to the conductivity of the liquid in the insulation loop tube 8. Therefore, the conductivity of the liquid is determined by measuring the electromotive current induced in the detection coil 7.

Although the electro-magnetic conductivity meter shown in FIG. 3 has an advantage that it is excellent in corrosion resistance since it will not cause polarization unlike the above-mentioned electrode method, it has a disadvantage that it can measure only liquids having a high conductivity. In order to enable to measure liquids having a low conductivity, it is necessary to increase the capacity of the coils, the input to the primary coil, the amplification of the detection coil output, the power source capacity and the like. Furthermore, the measuring apparatus will not only become complicated and expensive to manufacture, but also it hard to stably measure the conductivity not higher than 5,000 $\mu$S/cm since use of the above mentioned measure is limited in view of noises and other disturbance factors. Since it is necessary to form the tube through which an electromagnetically induced alternating current flows, the liquid flowing path will not only become complicated, but also there is till a serious problem that the shunt flow ratio should be maintained constant.

Therefore, the present invention was made to overcome the disadvantages of the prior art.

It is an object of the present invention to provide an electromagnetic conductivity meter which is simple in structure and is capable of stably measuring the conductivity of liquids having a concentration ranging from low to high and a method of measuring the conductivity of a liquid.

SUMMARY OF THE INVENTION

In order to accomplish the above mentioned object, the first aspect of the present invention provides an electromagnetic type conductivity meter comprising: a core; a primary coil wound around the core; an alternating power source for applying an alternating voltage having a given frequency to the primary coil to excite said core; a tube wound around the core through which a liquid to be measured flows; induction current detecting means disposed at the opposite ends of the tube; and an operational means for determining the conductivity of the liquid to be measured from a value of the induction current detected by the induction current detection means.

The second aspect of the present invention provides a method of measuring the conductivity of a liquid comprising the steps of; winding around a core a primary coil and a tube through which the liquid to be measured flows; applying an alternating voltage having a given frequency to the primary coil to excite the core for generating an induction current in the tube; and, determining the conductivity of the liquid to be measured.

The relation between the voltage and the number of turns in an electromagnetic induction circuit such as a transformer is generally represented by a formula (1).

$$V_1/V_2 = k \cdot N_1/N_2 \tag{1}$$

The formula (1) is transformed into formula (2).

$$V_2 = k \cdot N_1 \cdot V_1/N_2 \tag{2}$$

wherein V1 denotes a voltage across the primary coil 10; $V_2$ denotes a voltage across the secondary coil; $N_1$ denotes the number of turns of the primary coil 10; $N_2$ denotes the number of turns of the secondary coil; and "k" denotes a constant determined by the shape of the transformer, the sectional area of the coil, the material of the coil, etc.

Since $V_1$, $V_2$, $N_1$, $N_2$, and k are constant in the present apparatus, if they are represented as "K" and the constant related with the material of the secondary coil is represented as "m", the formula (2) is transformed into formula (3);

$$V_2 = K \cdot m \tag{3}$$

Since $m \propto S$, $V_2 \propto I_2$, $$I_2 = K_2 \cdot S \qquad (4)$$

wherein S denotes the conductivity of the liquid in the tube which forms the secondary coil; $I_2$ denotes the induction current flowing through the secondary coil; and $K_2$ denotes a constant, that is, it may be appreciated that the conductivity of the liquid in the tube 12 is proportional to the induction current flowing through the secondary coil.

In accordance with the present invention, an alternating voltage having a given frequency is applied to the primary coil wound around a core to excite the core so that an induction current flows through the tube. The conductivity of the liquid to be measured is determined from a measured value of the induction current.

DESCRIPTION OF PREFERRED EMBODIMENT

One embodiment of the present invention will be described in detail with reference to FIG. 1 and FIGS. 4-6.

Figure 1:
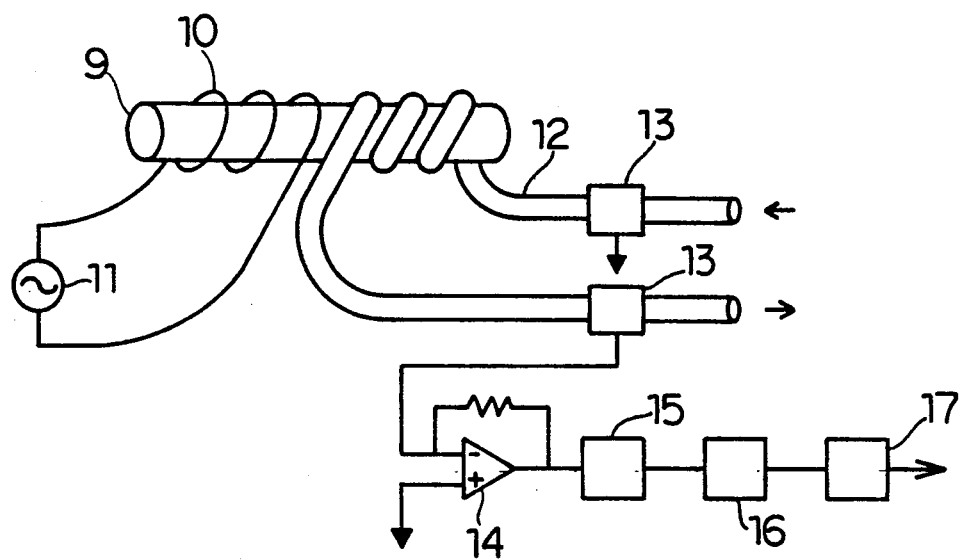
FIG. 1 is a schematic view showing an embodiment of an electromagnetic conductivity meter of the present invention.
Figure 2:
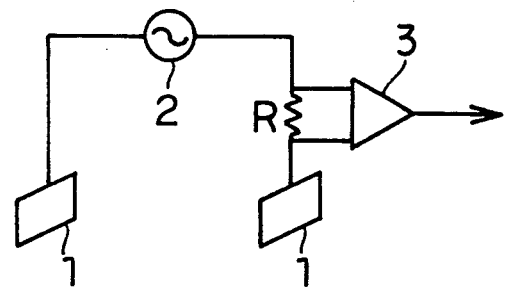
FIG. 2 is a schematic view for illustrating the principle of a prior art electrode type conductivity meter.
Figure 3:
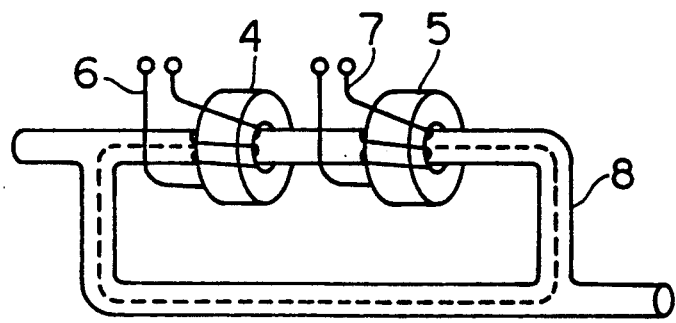
FIG. 3 is a schematic view illustrating the principle of a prior art electromagnetic conductivity meter.

In FIG. 1 a primary coil 10 having the number of turns $N_1$, is wound around a core 9 and is connected with an alternating power source 11. A tube 12 through which a liquid having a conductivity to be measured flows is wound around the core 9. The length of the tube 12 wound around the core 9 is proportional to the number of turns of the tube 12. That is, the length of the tube wound around the core 9 becomes long with increase in the number of turns $N_2$ and becomes short with decrease in the number of turns $N_2$. An electrode 13 is disposed at each of the opposite ends of the tube 12. Each of the electrodes 13 is in series connected with an operational amplifier 14, a range selection circuit 15 which is preset in accordance with the concentration of the liquid to be measured, a high frequency signal waveform processing circuit 16, and a circuit group 17 comprising a zerobalance circuit 44, a response circuit 42, a temperature compensation circuit 40.

Operation of the electromagnetic conductivity meter of the present invention will now be described.

An alternating voltage having a given frequency is applied to the primary coil 10 from the alternating power source 11.

As a result of this, an electromotive force is generated in the liquid to be measured in the tube 12. This electromotive force generates an induction current in the tube 12, which is then detected by the electrodes 13,13. The current detected by the electrodes 13 is proportional to the voltage V of the alternating power source 11 applied for exciting the core 9, the number of turns $N_1$ of the primary coil 10, the length $N_2$ (the number of turns) of the tube 12 through which the liquid to be measured flows and the conductivity of the liquid to be measured. Since the voltage V of the alternating power source 11, the number of turns $N_1$ of the primary coil 10 and the length $N_2$ of the tube 12 (the number of turns) are fixed as constants of the measuring instrument, the conductivity of the liquid to be measured is proportional to the value of the induction current.

Figure 4:
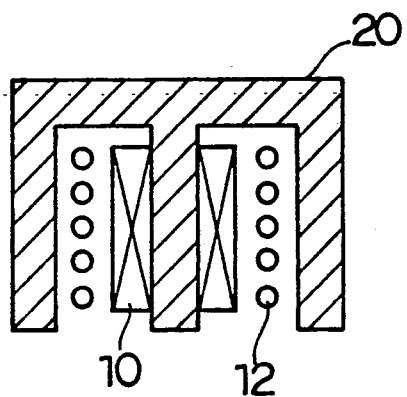
FIG. 4 is an end view of the concrete embodiment of the cell shown in FIG. 1.

It is preferable that $N_1$ and $N_2$ be about 100 and 5, respectively. It is also preferable that the frequency and the voltage of the alternating current applied to the primary coil 10 be about 1.5 kHz and 1.5 V, respectively. Since the conductivity changes with the temperature and specifically the change in temperature of 1, it is preferable that a temperature compensated sensor be disposed for reducing the influence of the temperature of the liquid to be measured. In the present embodiment, the temperature sensor is provided on a circuit in the vicinity of the cell, assuming that the temperature of the liquid to be measure is substantially equal to that of the cell. Although the structure of the cell is formed as shown in FIG. 1 for simplicity of the description of the invention, the cell may be specifically formed as shown in FIG. 4 so that the induction current may be effectively detected. Thus, the number of turns $N_1$ of the primary coil 10 and the number of turns $N_2$ of the tube 12 are wound around the central core of the ferrite member 20, concentrically.

Figure 5:
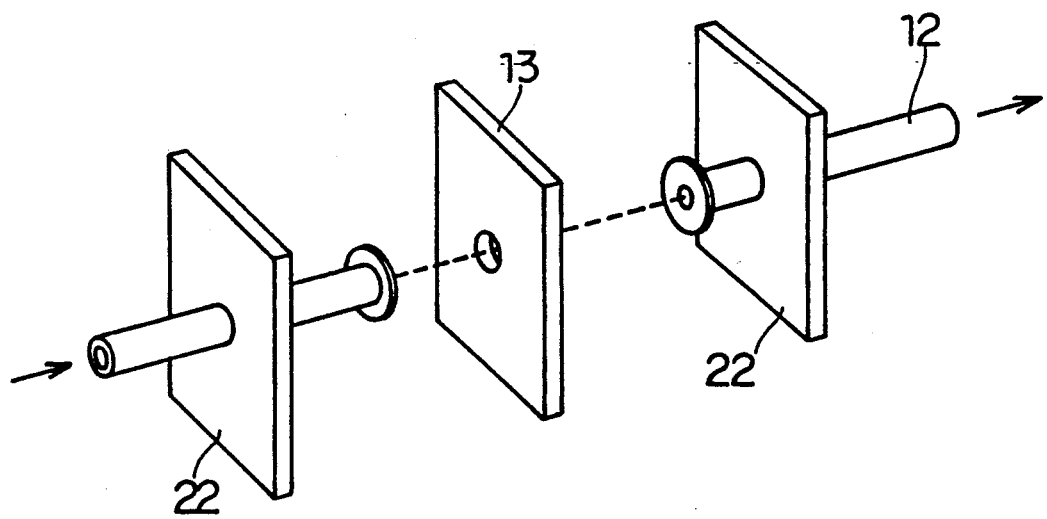
FIG. 5 is a perspective view for illustrating the concrete structure of the electrode.
Figure 6:
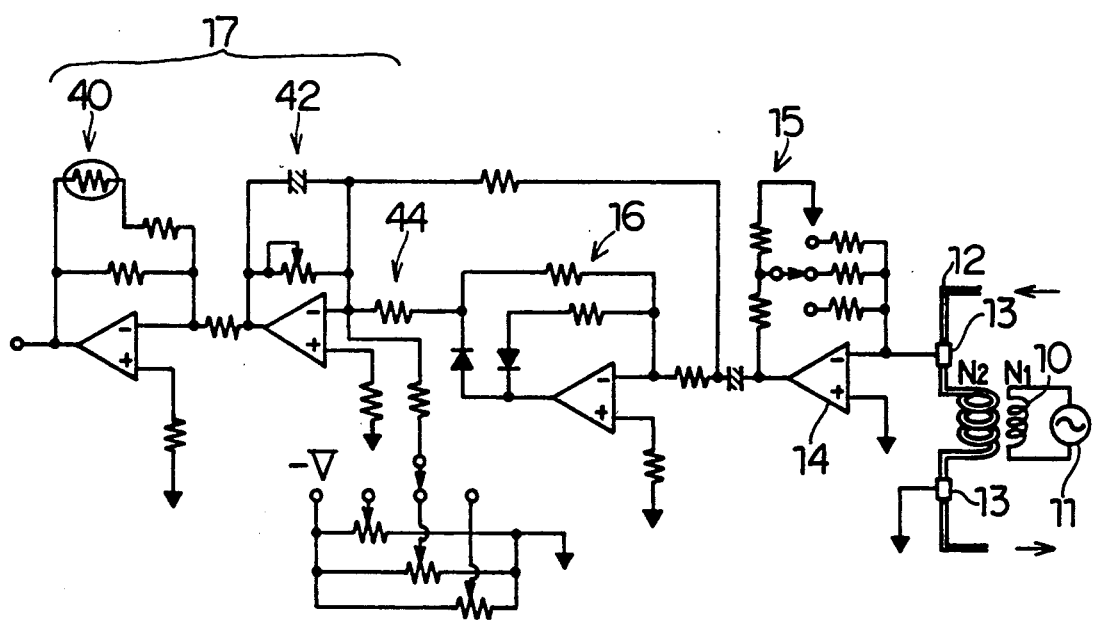
FIG. 6 is a schematic circuit diagram of operation cuicuit for the present invention.

The electrode may be specifically formed as shown in FIG. 5. A connection terminal of the electrode 13 is made of titanium which is bioinent. As shown in FIG. 5, the electrode 13 is sandwiched by a pair of the electrodes installation plates 22,22 through which the insulation tube 12 made of fluoroplastics passes.

These make it possible to stably measure the conductivity not higher than 1,000 μS/cm.

Therefore, the induction current detected by the electrode 13 is transformed into a voltage, which is amplified by an operational amplifier 14 and is successively passed through a range selection circuit 15 which is capable of selecting a range responsive to the density (conductivity) of the liquid to be measured; a high frequency signal processing circuit 16 which provides an analog signal which is a smoothed high frequency signal; and a circuit group 17 including a balanced circuit 44 which is capable of correcting the output depending upon the amplitude of the background noises, a response circuit 42 for electrically eliminating the noise, and a temperature compensation circuit 40 for automatically correcting the value of the conductivity depending upon a change in temperature of the cell. A signal is outputted from the circuit. The conductivity of the liquid to be measured is determined based on the outputted signal.

Since the influence of temperature cannot be neglected in order to measure conductivity at a high sensitivity, it is preferable to dispose a temperature compensation sensor (not shown) at induction current detecting portion to reduce the influence of the temperature of the liquid to be measured. This enables to stably measure even conductivity not higher than 1,000 μS/cm.

The present invention may be used for monitoring of the gradient of ion exchange, hydrophobic, affinity chromatography in a gradient effluent process of a liquid chromatography. For example, at what salt density a target protein is melted out may be directly and simply monitored.

Typical elution liquid includes phosphate buffer containing ammonium sulfate and acetate buffer containing sodium sulfate.

As mentioned above, in accordance with the present invention, an electromotive force induced in the tube can be detected as a signal of a high induction current by winding the tube through which the liquid to be measured around the core per se which is excited by the alternating voltage having a given frequency. This makes it possible to measure the conductivity of a liquid to be measured ranging from a low to high concentration. Since the tube is only wound around the core, the tube is simple so that a shunt effect can be eliminated.

What is claimed is:

1. An electromagnetic type conductivity meter comprising:
   a core;
   a primary coil wound around the core;
   an alternating power source for applying an alternating voltage having a given frequency to the primary coil to excite said core;
   a tube wound around the core through which a liquid to be measured flows;
   induction current detecting means disposed at the opposite ends of the tube; and
   an operational means for determining the conductivity of the liquid to be measured from a value of the induction current detected by the induction current detection means.

2. An electromagnetic conductivity meter as defined in claim 1 in which a temperature compensation thermistor is provided for compensating for change in conductivity of the liquid to be measured due to change in temperature thereof.

3. An electromagnetic conductivity meter as defined in claim 2 in which a range selection circuit is provided for adjusting an output of the meter in accordance with the concentration of the liquid to be measured.

4. A method of measuring the conductivity of a liquid comprising the steps of;
   winding around a core a primary coil and a tube through which the liquid to be measured flows;
   applying an alternating voltage having a given frequency to the primary coil to excite the core for generating an induction current in the tube; and,
   determining the conductivity of the liquid to be measured.

* * * * *